(12) United States Patent
Osypka

(10) Patent No.: US 9,925,370 B2
(45) Date of Patent: Mar. 27, 2018

(54) MYOCARDIAL HEART PACEMAKER ELECTRODE

(71) Applicant: Peter Osypka, Grenzach-Wyhlen (DE)

(72) Inventor: Peter Osypka, Grenzach-Wyhlen (DE)

( * ) Notice: Subject to any disclaimer, the term of this patent is extended or adjusted under 35 U.S.C. 154(b) by 0 days.

(21) Appl. No.: 14/379,786

(22) PCT Filed: Jan. 14, 2013

(86) PCT No.: PCT/DE2013/000016
§ 371 (c)(1),
(2) Date: Aug. 20, 2014

(87) PCT Pub. No.: WO2013/123924
PCT Pub. Date: Aug. 29, 2013

(65) Prior Publication Data
US 2016/0030733 A1 Feb. 4, 2016

(30) Foreign Application Priority Data
Feb. 24, 2012 (DE) .......................... 20 2012 001 945

(51) Int. Cl.
*A61N 1/05* (2006.01)
(52) U.S. Cl.
CPC .................................. *A61N 1/059* (2013.01)
(58) Field of Classification Search
CPC .... A61N 1/375; A61N 1/3956; A61N 1/0558; A61N 1/3754; A61N 1/3968;
(Continued)

(56) References Cited

U.S. PATENT DOCUMENTS

| 4,355,642 A | 10/1982 | Alferness |
| 4,413,636 A * | 11/1983 | Jasso ...................... A61N 1/056 607/122 |

(Continued)

FOREIGN PATENT DOCUMENTS

| DE | 2219044 A1 | 11/1972 |
| EP | 083674 A1 | 7/1983 |

(Continued)

OTHER PUBLICATIONS

International Search Report dated Jun. 6, 2013 in connection with PCT/DE2013/00016.

*Primary Examiner* — Deborah Malamud
(74) *Attorney, Agent, or Firm* — Locke Lord LLP; Scott D. Wofsy; Christopher J. Cillie

(57) ABSTRACT

The invention relates to a bipolar myocardial pacemaker electrode (1) consisting of a plug (2), a supply line (3), a cathode (4), an anode (5), surgical thread (7) and a fixation member (8), whereby the electrode (1) has an internal lumen and is freely movable on the thread (7); the thread (7) can be guided through the inner lumen of the electrode including the supply line and plug thereof, and distally supports the fixation member (8) in the form of a knot; the supply line (3) is externally insulated and has a distal cathode pole (4) tangentially arranged on the surface of the heart in the heart tissue (myocardium) in the usage position, wherein the cathode pole consists of a conically tapering coil and the supply line (3) has an anode pole (5) arranged proximally underneath the heart in the usage position.

7 Claims, 2 Drawing Sheets

(58) Field of Classification Search
CPC .... A61N 1/056; A61N 1/3758; A61N 1/0587; A61N 1/05; A61N 1/372; A61B 5/048; A61B 5/0538; A61B 2562/0209; A61M 2205/054
See application file for complete search history.

(56) References Cited

U.S. PATENT DOCUMENTS

| | | | |
|---|---|---|---|
| 5,716,392 A | 2/1998 | Bourgeois et al. | |
| 7,499,759 B2 * | 3/2009 | Coe | A61N 1/0587 607/126 |
| 7,920,928 B1 | 4/2011 | Yang et al. | |

FOREIGN PATENT DOCUMENTS

| | | |
|---|---|---|
| EP | 234457 A2 | 9/1987 |
| EP | 668087 A1 | 8/1995 |
| WO | WO-2005039691 A1 | 5/2005 |

* cited by examiner

MYOCARDIAL HEART PACEMAKER ELECTRODE

The invention relates to a bipolar myocardial permanent pacemaker electrode, especially suitable for children, with gentle fixation on the surface of the heart. In use the electrode pole is tangentially arranged on the surface of the heart in the heart tissue (myocardium) with a connection linking it to a pacemaker.

Myocardial pacemaker electrodes are already known from DE 2 219 044.9 from U.S. Pat. No. 4,355,642 and from WO 2005/039691.

Children born with a heart defect may require a pacemaker electrode after surgery. The known electrodes are too large compared to the children's heart size and may cause problems. For bipolar stimulation even two of these large electrodes often have to be attached to the baby's heart.

There is a need to provide a myocardial electrode as described above, in which the size and fixation of the electrode is adapted to a child's heart.

The invention relates to a bipolar myocardial pacemaker electrode (1) consisting of a plug (2), a supply line (3), a cathode (4), an anode (5), surgical thread (7) and a fixation member (8), whereby the electrode (1) has an internal lumen and is freely movable on the thread (7); the thread (7) can be guided through the inner lumen of the electrode including the supply line and plug thereof, and distally supports the fixation member (8) in the form of a knot; the supply line (3) is externally insulated and has a distal cathode pole (4) tangentially arranged on the surface of the heart in the heart tissue (myocardium) in the usage position, wherein the cathode pole consists of a conically tapering coil and the supply line (3) has an anode pole (5) arranged proximally underneath the heart in the usage position.

The surgical thread is inserted at the appropriate point in the myocardium using a heart needle. At the point at which the needle is drawn out of the myocardium a knot is made and the rest of the thread and needle is removed. The knot serves as a fixation member (barbed hook). The manufacturer has already guided the thread through the inner lumen of the electrode including its supply line and plug, so that the electrode is freely movable on the thread.

The pole of the electrode (cathode (4)) designed as a thin coil can now be easily drawn over the thread into the myocardium. The tread serves as a guide. The remaining thread protruding out of the electrode plug (2) is anchored in the plug pin. The anode (5) (indifferent pole) of the bipolar myocardial electrode is arranged proximally on the electrode supply line as a coil below the heart.

BENEFITS

The myocardial pacemaker electrode is fastened only by a small knot in a surgical thread and the anode is placed below the heart. There is no need for a second separate electrode as an anode. The electrode is easily movable on the thread, thus the cathode (4) can be optimally positioned.

DRAWINGS

Further details, features and benefits of the invention can be found in the following part of the description, in which the invention is explained in more detail using drawings. They drawings show the following in a schematic presentation.

FIG. 1 An execution example of the myocardial pacemaker electrode in which a surgical thread is inserted.

FIG. 2 An execution example of the myocardial pacemaker electrode in which a surgical thread is inserted into the myocardium.

FIG. 3 An execution example of the myocardial pacemaker electrode in which a knot is made using the surgical thread, the remaining thread is removed and the knot is pulled back to the outer wall of the heart.

FIG. 4 An execution example of the myocardial pacemaker electrode in which the electrode's distal pole (cathode) is drawn into the myocardium via the surgical thread.

FIG. 5 An execution example of the myocardial pacemaker electrode in which the proximal part of the surgical thread is anchored in the plug pin.

Figures 1, 2:
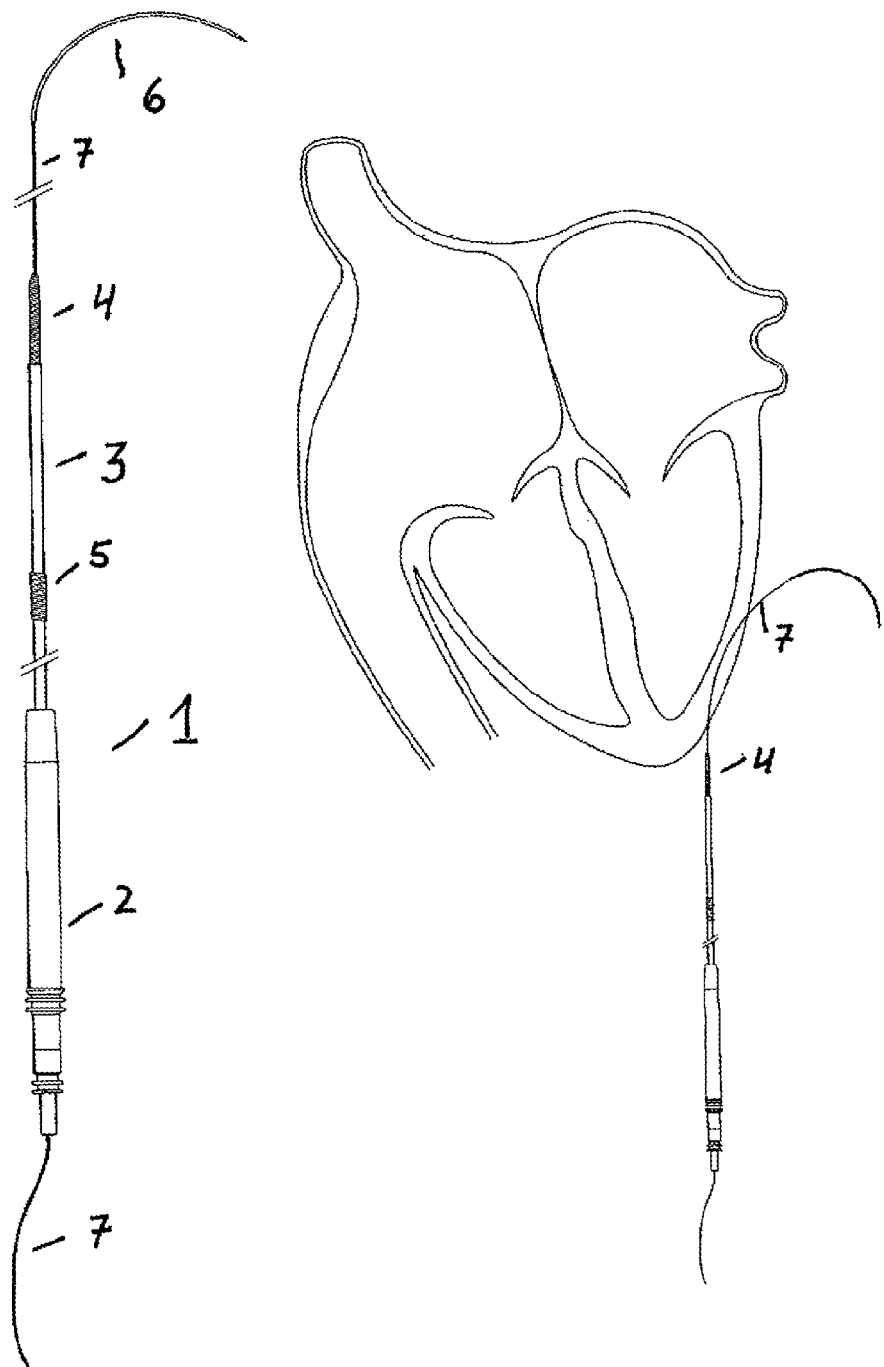
FIG. 1 shows an execution example of the myocardial pacemaker electrode (1) consisting of a plug (2), shaft tube or supply line (3), cathode (4), anode (5), heart needle (6) and the surgical thread (7), which runs through the entire length of the electrode.

The poles (cathode pole (4), anode pole (5)) are made of a biocompatible electrically conductive material. Examples mentioned are platinum, stainless steel or MP 35N.

The supply line (3) of the electrode (1) consists of a coil with at least two parallel wound insulated wires or of at least a coil and an insulated strand. The supply line (3) of the electrode (1) may also comprise at least two insulated strands. The supply line (3) must be insulated on the outside. The outer insulation of the line consists of a shaft tube of silicone or polyurethane, for example.

It is advantageous if the rest of the thread (7) is fastened. For this purpose the plug pin (10) has a slot in which the rest of the surgical thread can be fastened.

FIG. 2 shows an execution example of the myocardial pacemaker electrode (1) in which a surgical thread (7) is inserted through the myocardium. The cathode (4) is drawn into and positioned in the myocardium based on the fastening shown in FIG. 3 with the aid of the thread (7).

Figure 3:
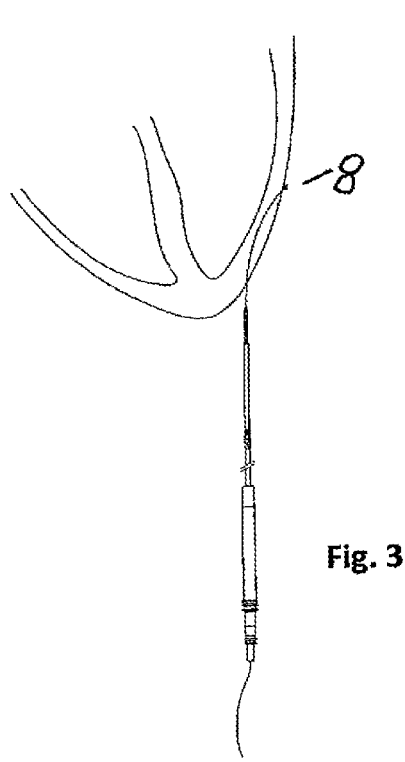

FIG. 3 shows an execution example of the myocardial pacemaker electrode (1) in which a knot (8) is made in the surgical thread (7), the remaining thread is removed and the knot has been drawn back to the outer wall of the heart.

Figure 4:
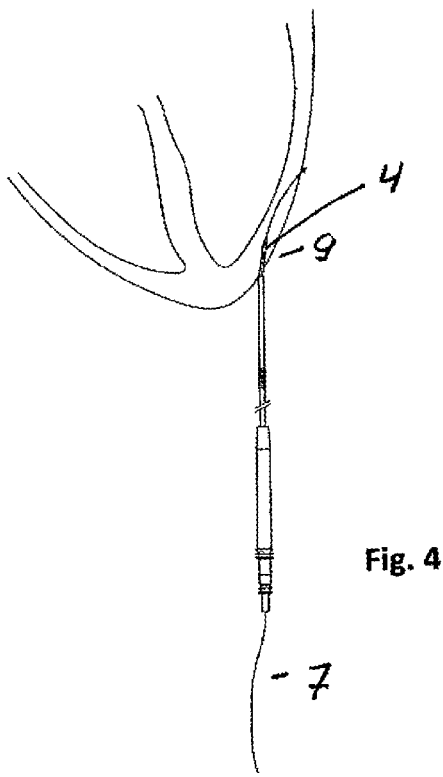

FIG. 4 shows an execution example of the myocardial pacemaker electrode (1) in which the distal pole (cathode) (4) of the electrode is inserted via the surgical thread (7) into the myocardium (9).

Figure 5:
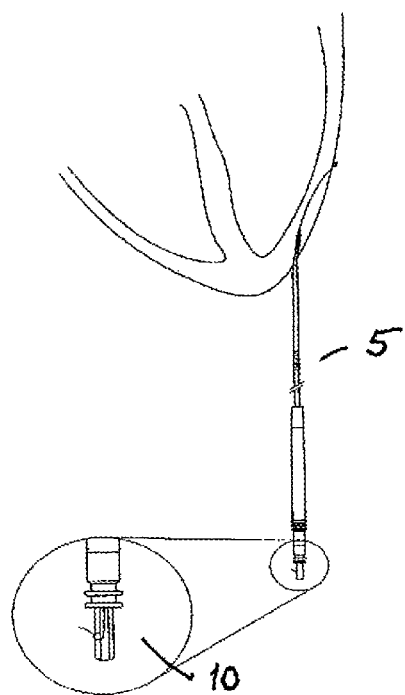

FIG. 5 shows an execution example of the myocardial pacemaker electrode (1) in which the proximal section of the surgical thread is anchored in the plug pin (10). The anode (5) of the electrode is formed into a coil and lies below the heart while in use.

The invention claimed is:

1. A bipolar myocardial pacemaker electrode having an internal lumen comprising:
   a plug with a plug pin, a supply line, a cathode, an anode, surgical thread running through the internal lumen of the electrode including the supply line and plug thereof and said surgical thread being distally connected to a heart needle configured to insert the surgical thread in the myocardium before the electrode with the internal lumen is guided over the thread being thus freely movable on the thread;
   wherein the surgical thread comprises a distally arranged fixation element in form of a knot and is configured to be distally knotted before the heart needle and the remaining thread is removed and before the electrode lead is drawn over the thread;

wherein the supply line is externally insulated, has a coil with at least two parallel wound insulated wires, and has a distal cathode pole configured for being tangentially arranged on the surface of the heart in the heart tissue in the usage position, wherein the cathode pole consists of a conically tapering coil and the supply line has an anode pole arranged proximally underneath the heart in the usage position.

2. The bipolar myocardial pacemaker electrode according to claim 1, wherein the poles are made of a biocompatible electrically conductive material.

3. The bipolar myocardial pacemaker electrode according to claim 2, wherein the biocompatible electrically conductive material includes at least one of platinum, stainless steel, or MP 35N.

4. The bipolar myocardial pacemaker electrode according to claim 1, wherein the supply line of the electrode consists of at least a coil and an insulated strand.

5. The bipolar myocardial pacemaker electrode according to claim 1, wherein the supply line of the electrode comprises at least two insulated strands.

6. The bipolar myocardial pacemaker electrode according to claim 1, wherein the external insulation of the supply line comprises a shaft tube of silicone or polyurethane.

7. The bipolar myocardial pacemaker electrode according to claim 1, wherein the plug pin has a slot, in which the rest of the surgical thread is configured to be fastened.

* * * * *